United States Patent [19]

Hammarström et al.

[11] Patent Number: 5,418,221
[45] Date of Patent: May 23, 1995

[54] COMPOSITION CONTAINING ENAMEL MATRIX FROM TOOTH GERMS FOR INDUCING BINDING BETWEEN LIVING MINERALIZED TISSUE PARTS

[75] Inventors: Lars Hammarström, Djursholm; Leif Blomlöf, Lidingö ; Sven Lindskog, Vårby, all of Sweden

[73] Assignee: Bioventures N.V., Curacao, Netherlands Antilles

[21] Appl. No.: 217,024

[22] Filed: Mar. 24, 1994

Related U.S. Application Data

[63] Continuation of Ser. No. 645,347, Jan. 23, 1991, abandoned, which is a continuation of Ser. No. 94,889, Sep. 10, 1987, abandoned.

[30] Foreign Application Priority Data

Sep. 25, 1986 [SE] Sweden .................................. 8604069

[51] Int. Cl.$^6$ ...................... A61K 37/00; A61K 6/00; A61F 13/00; C12N 5/00
[52] U.S. Cl. ..................................... 514/21; 424/435; 433/215; 433/217.1; 435/1; 435/240.2; 514/900; 623/16; 623/18
[58] Field of Search .................. 435/1, 240.2; 433/215, 433/226, 228.1, 217.1; 604/54; 424/435; 514/21, 835, 900; 623/16, 18

[56] References Cited

U.S. PATENT DOCUMENTS

| | | | |
|---|---|---|---|
| 4,702,734 | 10/1987 | Terranova | 604/54 |
| 4,728,331 | 3/1988 | Russier | 623/16 |

OTHER PUBLICATIONS

Copenhauer et al. *Bailey's Textbook of Histology*. Williams and Wilkens Co. Baltimore. p. 467, 1978.
Junqueira et al, *Basic Histology*, "The Teeth and Associated Structures", pp. 284-288, 1977.

*Primary Examiner*—David M. Naff
*Attorney, Agent, or Firm*—Oblon, Spivak, McClelland, Maier & Neustadt

[57] ABSTRACT

Binding between parts of living mineralized tissue such as between a tooth and the jaw bone is induced with a composition containing mammalian enamel matrix isolated from tooth germs and a carrier such as water, and optionally an adhesive containing fibrinogen, factor XIII and thrombin. The enamel matrix is a precursor to tooth enamel and induces binding by forming cementum tissue. The enamel matrix may be obtained from bovine or porcine species. The composition is particularly applicable in dental therapies including loosening of teeth due to periodontitis, transplantation of teeth or in reintroduction of teeth disconnected by accident. The composition may also be used for healing of artificial implants such as tooth implants and implants of skeletal replacements such as artificial hip joints. In the case of a dislocated tooth, the composition is applied to a surface of the tooth root and the tooth is put back into its alveolus and lightly fixed for some weeks. In the treatment of periodontitis, a tooth root surface is exposed by incision, the surface is cleaned, the composition is applied to the cleaned root surface and the incision is closed and optionally stitched to promote healing.

14 Claims, 3 Drawing Sheets

COMPOSITION CONTAINING ENAMEL MATRIX FROM TOOTH GERMS FOR INDUCING BINDING BETWEEN LIVING MINERALIZED TISSUE PARTS

This application is a continuation of application Ser. No. 07/645,347, filed on Jan. 23, 1991, now abandoned, which was a Continuation of application Ser. No. 07/094,889, filed on Aug. 10, 1987, also abandoned.

The present invention relates to a composition for use in inducing binding between parts of living mineralized tissue by new formation of mineralized tissue on at least one of the parts but possibly also on the other part. The invention also relates to a process for inducing such binding, for example for the treatment of periodontitis.

The present invention relates to new biologically based techniques useful with regard to inducing binding between parts of mineralized tissue, for example bone. Even if the invention is generally applicable to provide for such binding it will, in the present disclosure, be illustrated mainly in connection with the treatment of loosening teeth, so called periodontitis, However, it should be noted that this principal illustration of the invention must not be interpreted in a limiting manner. Before the techniques of the invention are described more closely it is suitable, in order to facilitate understanding of the invention, to give a brief background to the biological conditions in connection with teeth and associated disorders. At normal dental status the teeth are anchored in special cavities, so called alveoli, in the jaw bone. Between the roots of the teeth and the jaw bone a so called periodontal membrane is located. The roots of the teeth are mainly constituted by a material called dentin. This dentin is peripherally covered by a thin layer of cementum, thickness about 0.01 to 1 mm. In this cementum inter alia collagen fibers are found which extend from the cementum through the periodontal membrane and which are anchored in the jaw bone. Thus, the cementum is extremely important for the attachment of a tooth to the jaw bone. The periodontal membrane has a thickness of about 0.2 mm and consists of the above-mentioned collagen fibers and vessels and nerves lying between said fibers and cells belonging to these tissues.

The jaw bone does not extend all the way up to the crown of the tooth, and in the part of the root which is not covered by jaw bone fibers from the root cementum extend out into the surrounding tooth gum, the gingiva. These fibers assist in anchoring the tooth and, furthermore, stabilize the tooth gum. The tooth gum, as well as the whole oral cavity, is covered by a thin layer of epithelium. This epithelium forms a dense collar or sleeve around the teeth. Adjacent to the teeth there is formed a shallow furrow between the teeth and the epithelium.

Inflammatory disorders in the tissues attaching the teeth to the jaw bone are quite frequent and strike to a varying extend the major part of the population all over the world. The methods of treatment hitherto used are mainly aiming at retarding an ongoing disease process and at preventing loosening of the teeth as far as possible. Presently, no clinically applicable method exists having the ability of providing healing in such a manner as to enable the teeth to regain attachment to the jaw bone.

A partial problem within this area is the cases where the patients have a congenital defect in the dental attachment. Such patients develop symptoms of periodontitis at an early age, so called juvenil periodontitis. The treatment often involves extraction of the tooth and replacement with some bridge construction at a substantial cost.

The bacteria on the surface of the teeth cause chronic inflammation in the tooth gum around the teeth. Inflammatory cells excrete their decomposing enzymes which are intended for the bacteria, but in this case they attack the collagen fibers attaching the tooth to gingiva and jaw bone. The cells on the surface of the tooth root or the cementum are subject to destruction and epithelium from the oral mucous membrane grows downwardly along the teeth and produces a so called gingival crevice. In this crevice new bacteria obtain a protected area where they can grow. New inflammatory cells are collecting in said area, and the decomposition of the tissues of the periodontal membrane proceeds. The cementum cells succumb and the bone of the alveolar area is destroyed. The process proceeds generally very slowly but can at intervals proceed very fast. After some time the teeth subject to attack will completely lose their attachment to the jaw bone.

Today's treatment is principally directed at removing the bacterial deposits on the tooth surfaces. When the bacteria are removed the inflammation in the gingiva and the periodontal membrane ceases and the decomposition process comes to a stop. The treatment also aims to preventing new bacterial deposits to form on the dental surface. Thus, the treatment results in ending the destruction of the attachment of the teeth to the jaw bone, but no new periodontal membrane or new cementum will be formed in the healing.

In connection with the research forming the basis of the present invention it has now somewhat surprisingly been found that the formation of cementum is initiated by a thin layer of a precursor to enamel which, in development of the root is formed along all of the root surface. This layer of enamel seems to affect collagen fibre cells in the area so that they develop to cells forming cementum. The thin layer of enamel seems to disappear to a great extent in the continued development of the cementum, but in certain areas remaining residues can be observed.

In connection with investigations made, it has been found that if dentin is exposed to the cells of the periodontal membrane, for example by grinding a cavity in the surface of the root, healing takes place in the form of a bone-like tissue i.a. lacking the fibers attaching the tooth to the surrounding tissues. If, however, the generated cavity is covered with a precursor to enamel, in the following called enamel matrix, it is found that normal cementum tissue is generated. In the introductory experiments endogenous enamel matrix was used, but it was later found that the same favorable results were obtained using enamel matrix from a totally different animal species. Thus, it has been found in experiments on monkeys that one can induce formation of cementum by covering a cavity ground in the surface of the root with enamel matrix of, for example porcine origin.

By the following invention there is thus provided new techniques for inducing binding between parts of living mineralized tissue by renewed formation of mineralized tissue on at least one of the parts, and these techniques are characterized by the application of a precursor to enamel, so called enamel matrix for the induction of binding. Thus, the invention provides a composition for such use and said composition contains as an active constituent such enamel matrix.

As previously indicated the invention is particularly applicable in connection with dental therapies, for example for the treatment of periodontitis, i.e. loosening of teeth, in transplantation of teeth or in reintroduction of teeth disconnected by accident. However, the invention can be used also to facilitate healing of artificial implants, for example tooth implants, implants of skeletal replacements such as artificial hip joints. The invention may also be used to induce formation of mineralized tissue on such skeletal replacements where it is desired to provide for a new tendon attachment. The enamel matrix used in applying the techniques according to the present invention is suitably obtained from some mammal the teeth of which are under development. A suitable source of the enamel matrix is slaughtered animals, for example pigs or calves, the sacrifice of which often takes place while the teeth still are under development, in the case of pigs for slaughter an age of about half a year. Preferred mammals are thus selected from bovine or porcine species (i.e. cattle or pig) but also other species are conceivable, for example sheep and rodents which have continuously growing teeth.

The composition according to the invention may consist of only such enamel matrix, suitably admixed with water, but the composition may also contain the enamel matrix in combination with a carrier, diluent or adhesive acceptable for the purpose. For dental use it is suitable that the carrier or diluent is dentally acceptable. The composition may optionally contain stabilizers or preserving agents for the purpose of increasing storage stability. Solely the dental matrix in combination with water can, however, be stored in the cold for a certain period of time up to the actual use.

The invention provides a process for the treatment of periodontitis involving regaining attachment of the teeth by inducing a formation of root cementum and jaw bone and a physiological collagen fiber attachment between these. The process is characterized in that epithelium, if present, is removed from the root of the tooth and the root is then supplied with a layer of precursor to dental enamel, so called enamel matrix.

In the preferred application of the invention for the treatment of periodontitis the area of a tooth subject to attack is subjected to incision to expose the surface of the root while removing possibly formed epithelium, the clean surface of the root is then coated with a layer of enamel matrix or a composition containing such enamel matrix as an active constituent, after which the collagen tissue is repositioned and optionally stitched so that healing can take place.

As previously mentioned the invention can be used, in addition to the treatment of periodontitis, in replantation or transplantation of teeth. It is relatively frequent that youths in their lower teenage are subject to accidents which result in dislocation of one or several teeth. This is mainly the case with the front teeth. By quickly putting back the dislocated teeth good healing can be obtained with normal attachment to the jaw bone. In many cases such reinstatement of dislocated teeth cannot be carried out within a reasonable period of time, but the teeth must be kept for a period of time in an unsuitable medium outside the mouth, for example in the free air. The cells of the periodontal membrane on the surface of the root will then have been destroyed, and when the tooth is put back in location in the mouth it will not regain a physiological attachment but fall out after a certain period of time. Up to now no method has been deviced by which one can obtain regeneration of a new attachment.

In accordance with the techniques of the invention the dead periodontal membrane on the dislocated tooth may, however, be removed in a suitable manner, which can be mechanical or chemical, and the composition of enamel matrix is then applied to the naked surface of the root. The tooth is then put back into its alveolus and lightly fixed for some weeks. Due to the new enamel matrix on the surface of the root a new cementum layer will be generated and the tooth will hereby obtain new attachment.

In regard to the transplantation of teeth, i.e. transfer of teeth from one individual to another, it has been found that the tissues of transplanted teeth are attacked by the immune defense of the receiver and decomposed in a very short period of time. Attempts have been made to carry out transplantation between immunologically suitable individuals. Also these attempts have, however, been discouraging. Neither has it been considered reasonable to resort to long term treatment with pharmacological preparations suppressing the rejection reaction for the purpose of maintaining one or several transplanted teeth. Thus, there is today no clinically useful method for transplantation of teeth leading to a favorable long term prognosis.

However, by employing the techniques according to the present invention the problem can be solved by removing the teeth to be transplanted from the donor, removing the dental pulp, cleaning the pulp space and applying the root filler agent in the pulp space. The periodontal membrane is mechanically or chemically removed and the root of the tooth is covered with the composition containing enamel matrix. Then the tooth is placed in its new location in the receiver's mouth. The tooth is maintained in a fixed position for a short period of time, and due to the enamel matrix, reformation of endogeneous mineralized tissue which covers the transplanted tooth and provides fixation of same will be induced.

According to a further preferred aspect of this invention the enamel matrix composition may be supplemented with a tissue adhesive based on fibrinogen, Factor XIII (which is a plasma-derived coagulation factor) and thrombin. Such supplemented composition may be constituted by a premix of enamel matrix and fibrinogen and Factor XIII, the thrombin being added immediately before applying the composition to the surgical site. The premix may optionally contain aprotinin to reduce the rate of decomposition. A preferred commercial product for use in such supplemented composition is Tisseel ®, a two-component fibrin sealant manufactured and sold by IMMUNO AG, Vienna, Austria.

In using such tissue adhesive the premix of enamel matrix, fibrinogen, Factor XIII and, optionally, aprotinin, is mixed with a thrombin solution, and the resulting composition is then rapidly applied to the surgical site. In the treatment of periodontitis this technique greatly facilitates surgery. Thus, the adhesion of the composition to the root is enhanced, bleeding is stopped and positioning of the muco-periosteal flap is greatly simplified while eliminating the use of sutures.

The invention will in the following be further illustrated in conjunction with specific examples. The exemplification is made in connection with dental experiments performed on rats, monkeys and humans. The exemplification is made in connection with the appended drawing, wherein.

FIG. 1 shows a detail of a cross section through a root of a tooth with adjoining tissues from a monkey;

Figure 1:
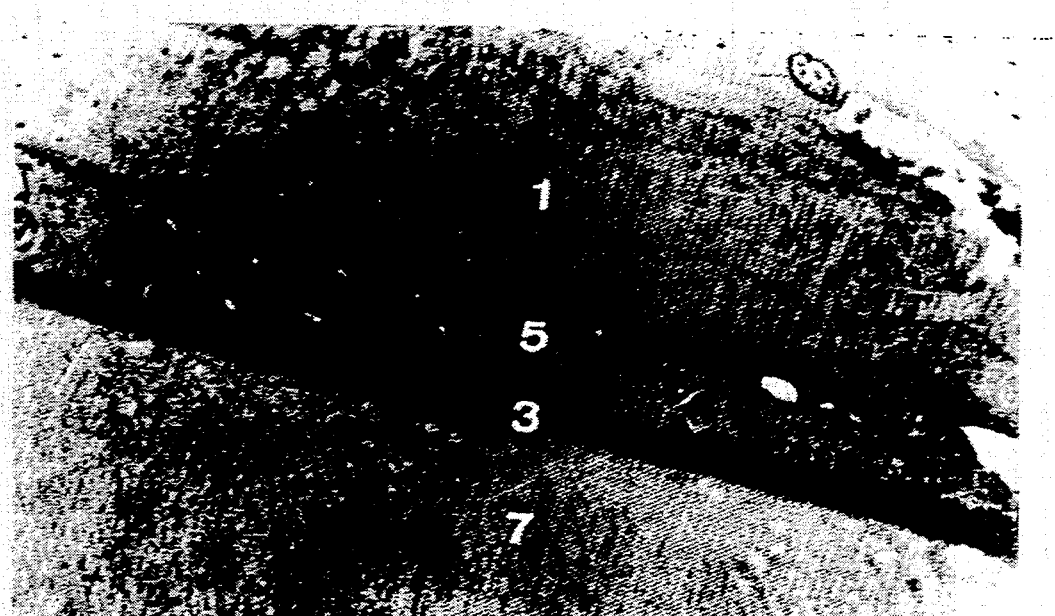

The detail blowup shown in FIG. 1 illustrates a cross section through a root of a tooth with adjoining tissues from a monkey tooth which is normally and naturally attached to the jaw bone. Between jaw bone 1, wherein the teeth are attached, and root 7 of the tooth, the dentin, the so called cementum 3 and the periodontal membrane 5 providing fixation of the tooth to the jaw bone 1 are found adjacent to root 7 of the tooth.

EXAMPLES

In the following examples there is used as a treating composition a precursor to enamel, i.e. enamel precursor or enamel matrix, tissue obtained from pigs for slaughter sacrificed at an age of about 6 months and thus provided with teeth under development. From cleaned pig jaws the tooth germs are isolated. These germs are constituted by enamel matrix producing cells (the enamel organ), enamel matrix, dentin, odontoblasts and dental papille. The tooth germs freed of the enamel organ are scraped to isolate and recover the desired enamel matrix, a semi-solid white mass being obtained which is homogenized with water to form a whipped cream-like consistency. The homogenizer used is a so called polytron manufactured by Kinematica GmbH, Luzern, Switzerland. The composition obtained is then used in the following examples.

EXAMPLE 1

A tooth is extracted from a monkey and is then stored in air for one hour, the periodontal membrane being then removed. On the root of the tooth there is then applied a thin layer of enamel matrix from pig manufactured as above, the tooth being then repositioned in its location in the jaw bone.

Figure 2:
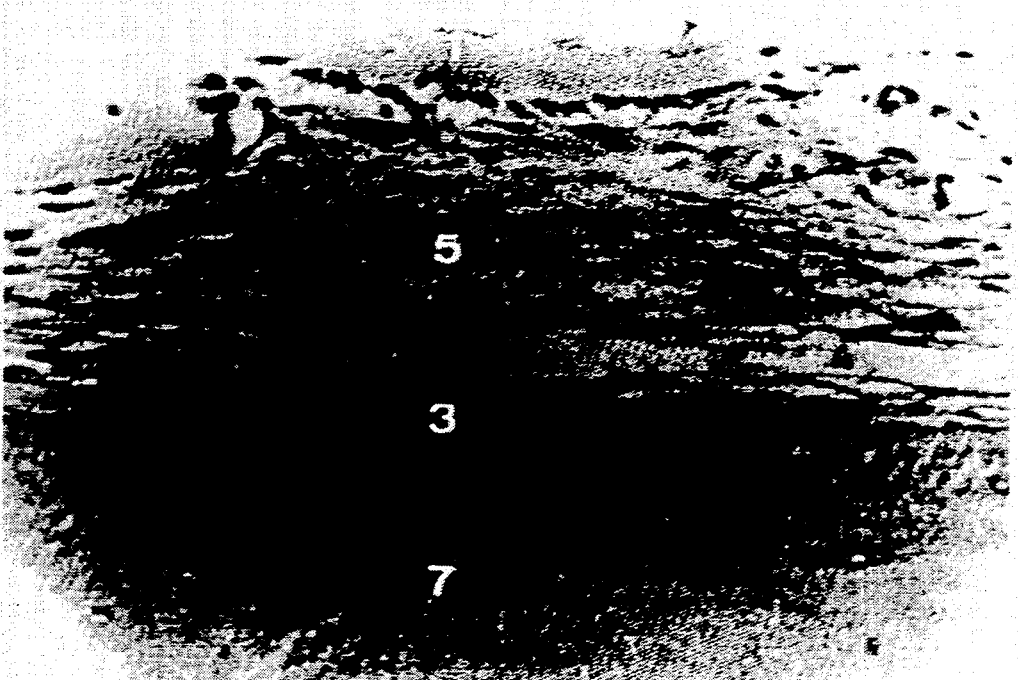
FIG. 2 shows a detail of a cross section of the root of a tooth from a monkey treated in accordance with the invention.

In FIG. 2 there is shown how after a few weeks a new periodontal membrane 5 has been regenerated between jaw bone 1 and root 7 of the tooth, and also a new cementum layer 3 has been formed between the periodontal membrane 5 and the root 7 of the tooth. Due to the use of the composition according to the present invention the replantation of the monkey tooth has thus been carried out successfully with complete renewed anchorage of the tooth in the jaw bone.

EXAMPLE 2

Figure 3:
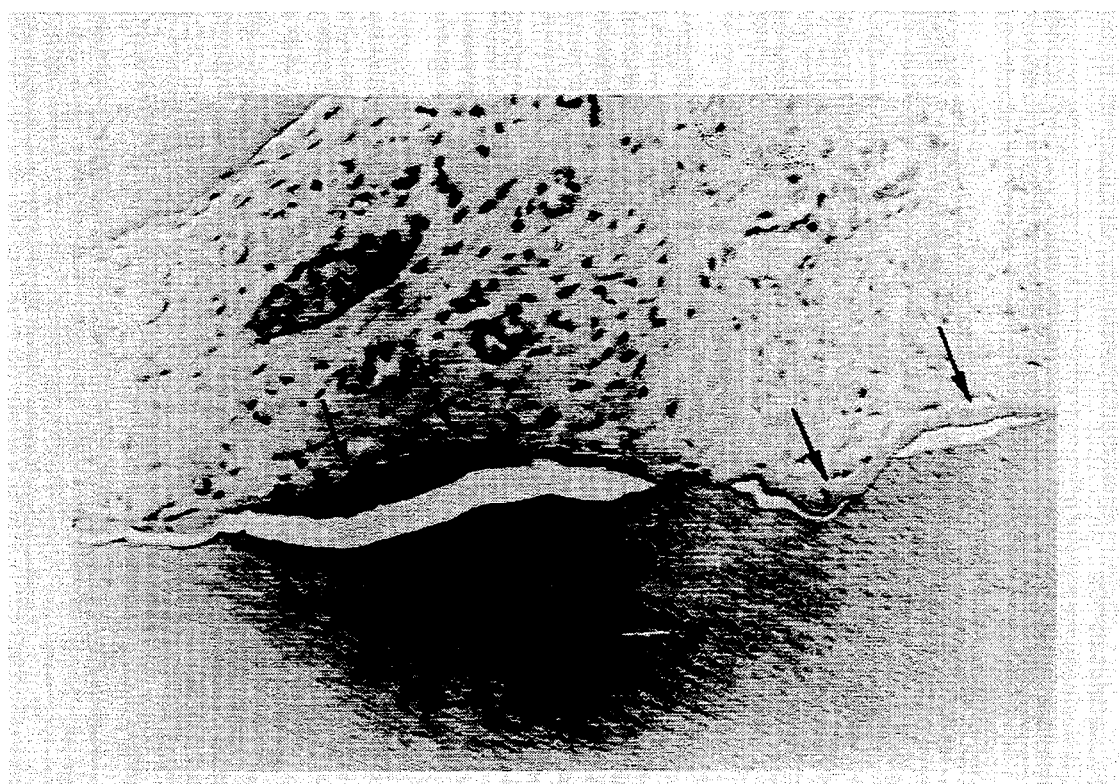
FIG. 3 shows a detail of a replanted monkey tooth without treatment.

This example is a comparison between healing of a cavity ground in a monkey tooth with and without treatment while using the techniques according to the present invention. In FIG. 3 there is shown a detail blowup of the area between jaw bone 1 and root 7 of a monkey tooth. This tooth has been first extracted, then a cavity has been ground on the surface of the root and the tooth has then been put back in its location in the jaw bone for healing. The enlargement according to FIG. 3 shows the healing after 8 weeks, and as is seen only small areas of bone-like mineralized tissue have been formed (see the curved arrows).

Figure 4:
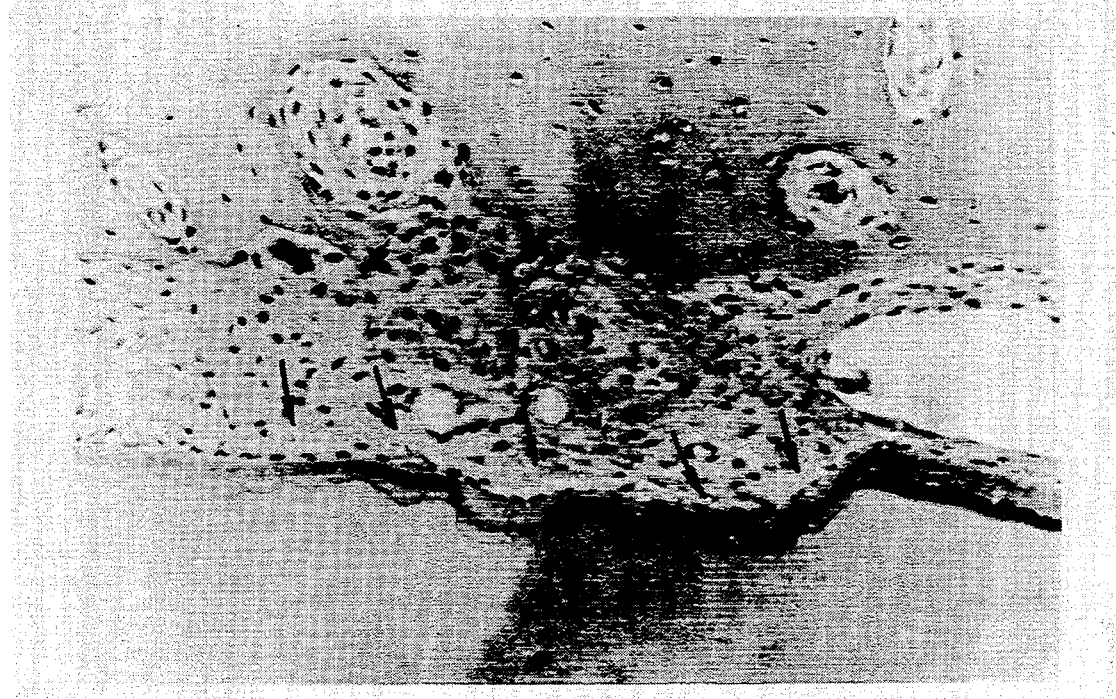
FIG. 4 shows a corresponding detail but on a tooth treated in accordance with the invention.

In FIG. 4 there is shown an experiment carried out in the same manner but where the generated cavity has been filled with the composition prepared according to the above before putting back the tooth. Also here the healing after 8 weeks is shown, and it is clear from the figure how well the periodontal membrane 5 has healed. The figure also shows how new cementum 3 has been formed in the cavity (cf. the non-filled arrows).

EXAMPLE 3

The purpose of this example is to show the influence of "the attachment-promoting composition" on healing of experimental marginal periodontal wounds. Experimental defects in the marginal periodontium of monkey teeth were created by removing dental cementum, periodontal membrane and marginal alveolar bone to a cervico-apical distance of approximately 5 mm with a dental bur. The composition was then applied to the experimental defects and the area allowed to heal. Control defects were also prepared but allowed to heal without the application of the composition. After a healing period the results were evaluated histologically.

The results show that healing, in a way similar to the results described in the previous examples was obtained only when the composition had been applied. This comprised the formation of an adhering layer of new cementum, periodontal membrane and alveolar bone. Thus, new attachment had resulted. This was not the case for the control teeth where the defect persisted only to have been covered with oral epithelium. These results indicate an application of the composition in the treatment of periodontitis.

EXAMPLE 4

This example shows the influence of "the attachment-promoting composition" on marginal periodontal healing following treatment of periodontitis in an experimental animal. Monkeys with naturally occuring periodontitis were selected for the experiment. They received conventional periodontal surgery after which one experimental side in each animal was treated with application of the composition on the exposed root surfaces. The other side served as a control. After a healing period the results were evaluated histomorphometrically.

The results showed that, after application of the composition a new marginal attachment had been created, consisting of new adhering cementum, periodontal membrane and alveolar bone up to a level corresponding to the enamel-cementum border. In figures this means several millimeters of new periodontal attachment. The control teeth only showed insignificant and inconsistent gain of new attachment without any new cementum. These results indicate an application for the composition in the treatment of periodontitis also in man.

EXAMPLE 5

The purpose of this example is to show the influence of "the attachment-promoting composition" on marginal periodontitis in man. After approval from The Swedish Medical Board and The Regional Ethics Comittee the composition was used as an adjunct to conventional surgical treatment of patients with marginal periodontitis. The patients were operated on and dental calculus and granulation tissue were removed. The composition was "painted" on the naked root surfaces and covered with a muco-periostal flap. The healing results were evaluated by periodical clinical inspection, recording of pocket depth and ingival index as well as examination of intra-oral radiographs. The results after application of the composition was compared with previous quantitative studies on conventional periodontal surgery.

Figure 5:
FIG. 5 shows an intra-oral radiograph taken before surgery.
Figure 6:
FIG. 6 shows a corresponding radiograph taken after surgery.

The results showed that the composition had promoted a significant increase of marginal alveolar bone height (FIGS. 5 and 6). These figures show intra-oral radiographs taken before (FIG. 5) and 6 months after (FIG. 6) periodontal surgery involving the application of "the attachment-promoting composition" The preoperative radiograph (FIG. 5) shows that the level (arrow) of the alveolar bone (1) is situated almost at the apex of the tooth. Six months after the application of the composition (FIG. 6) a significant amount of new alveolar bone (1) has been formed and the level is indicated by an arrow at mid-root and is raised by several millimeters. Such a healing result has never been seen after conventional periodontal surgery. Healing in general appeared to progress more rapidly both regarding clinical appearance and reduction of marginal pocket depths compared with previous studies on conventional periodontal surgery. These results show that the composition also has the ability to promote new periodontal attachment in man, a healing result not seen with conventional treatments.

EXAMPLE 8

This example illustrates an improved method of application of "the attachment-promoting composition" in clinical practice. Patients with marginal periodontitis were treated as described in Example 5 with the only difference that a fibrin-based tissue adhesive was mixed in with the composition. The tissue adhesive is composed of fibrinogen, plasma-fibronectin, Factor XIII (a plasma-derived coagulation factor), plasminogen, aprotinin, thrombin and calcium chloride and manufactured by IMMUNO AG, Vienna, Austria. The tissue adhesive marketed under the name of Tisseel or Tissucol polymerizes after its various components have been mixed together to form an adhering coagulum. Thus, the addition of Tisseel (Tissucol) to "the attachment-promoting composition" enhances adhesion to the root surfaces during periodontal surgery. Furthermore, bleeding is stopped, facilitating visibility and positioning of the muco-periosteal flap. The flap can also be positioned more cervically on the root surfaces and sutures can be eliminated. Covering the root surfaces is essential for the healing results since this ultimately determines the degree of new attachment.

EXAMPLE 7

The purpose of this example is to describe the mineralized tissue-inductive capacity of "the attachment-promoting composition" The composition was placed in gelatin capsules which were operated into the abdominal muscle in rats. Sham operated rats were used as control. After a healing period the rats were killed and the tissue reaction in the operated areas was evaluated with radiographs, histology and incorporation of $^{45}$Ca.

The results showed that a mineralized tissue, resembling cementum had been formed following the application of the composition. No traces of any newly formed tissue were seen in the sham operated animals.

The experiments presented above show unambiguously the practical application and advantages of the present invention. In view of the fact that enamel matrix from pig has been used in experiments performed on monkeys the tests additionally show that it is not necessary to use an endogenous enamel matrix. This latter finding is, of course, a substantial advantage since it means that easy access to raw material can be ensured.

We claim:

1. A composition for use in inducing binding between parts of living mineralized tissue by regeneration of mineralized tissue on at least one part of the parts, comprising an effective binding amount of a material consisting essentially of mammalian enamel matrix isolated from tooth germs and a carrier acceptable for inducing said binding, said enamel matrix being a precursor to tooth enamel and inducing binding by forming cementum tissue.

2. The composition of claim 1, wherein said mammalian enamel matrix originates from a bovine or porcine species.

3. The composition of claim 1, wherein said composition further contains an adhesive which consists essentially of fibrinogen, factor XIII, and thrombin.

4. The composition of claim 1, wherein said carrier consists essentially of water.

5. A process for inducing binding between parts of living mineralized tissue by regeneration of mineralized tissue on at least one of the parts, comprising applying to at least one of said parts, a layer of a composition comprising an effective binding amount of a material consisting essentially of mammalian enamel matrix isolated from tooth germs and a carrier acceptable for inducing said binding, said enamel matrix being a precursor to tooth enamel and inducing binding by forming cementum tissue;
adjoining said parts so as to enable binding with the formation of cementum and the regeneration of mineralized tissue.

6. The process of claim 5, further comprising removing soft tissue from a joint site of at least one of said parts, before applying said composition to at least one of said parts.

7. The process of claim 5, wherein said mammalian enamel matrix originates from a bovine or porcine species.

8. The process of claim 5, wherein said composition further contains an adhesive which consists essentially of fibrinogen, factor XIII, and thrombin.

9. The process of claim 5, wherein said carrier consists essentially of water.

10. A process for the treatment of periodontitis, comprising exposing an area of the root surface of a tooth by incision to form a muco-periostal flap, removing any pocket epithelium present, coating the exposed surface area of said root with a layer of a composition comprising an effective binding amount of a material consisting essentially of mammalian enamel matrix isolated from tooth germs and a carrier acceptable for inducing said binding, said enamel matrix being a precursor to tooth enamel and inducing binding by forming cementum tissue and repositioning said muco-periostal flap and allowing binding to occur by said enamel matrix forming cementum tissue.

11. The process of claim 10, further comprising stitching said muco-periostal flap to permit healing.

12. The process of claim 10, wherein said mammalian enamel matrix originates from a bovine or porcine species.

13. The process of claim 10, wherein said composition further contains an adhesive which consists essentially of fibrinogen, factor XIII, and thrombin.

14. The process of claim 10, wherein said carrier consists essentially of water.

* * * * *